(12) United States Patent
Zgoda et al.

(10) Patent No.: US 7,036,510 B2
(45) Date of Patent: May 2, 2006

(54) PERCUTANEOUS TRACHEOSTOMY BALLOON APPARATUS

(75) Inventors: Michael A. Zgoda, Lexington, KY (US); Andrew K. Hoffa, Bloomington, IN (US); Laura Rice, Westfield, IN (US)

(73) Assignee: Cook Critical Care Incorporated, Bloomington, IN (US)

( * ) Notice: Subject to any disclaimer, the term of this patent is extended or adjusted under 35 U.S.C. 154(b) by 59 days.

(21) Appl. No.: 10/833,872

(22) Filed: Apr. 28, 2004

(65) Prior Publication Data

US 2004/0255954 A1 Dec. 23, 2004

Related U.S. Application Data

(60) Provisional application No. 60/465,973, filed on Apr. 28, 2003.

(51) Int. Cl.
*A61M 16/00* (2006.01)
*A61M 29/00* (2006.01)

(52) U.S. Cl. .......................... 128/207.29; 128/207.14; 604/69.01

(58) Field of Classification Search ........... 128/200.24, 128/200.26, 207.14, 207.15, 207.29, 200.29; 606/191, 192, 194, 108, 198; 604/96.01, 604/160, 161, 264, 272
See application file for complete search history.

(56) References Cited

U.S. PATENT DOCUMENTS

| | | | | |
|---|---|---|---|---|
| 4,248,236 A | * | 2/1981 | Linder | 604/100.01 |
| 5,058,580 A | * | 10/1991 | Hazard | 128/207.15 |
| 5,507,279 A | * | 4/1996 | Fortune et al. | 128/200.26 |
| 5,515,844 A | * | 5/1996 | Christopher | 128/200.26 |
| 5,653,230 A | | 8/1997 | Ciaglia et al. | |
| 5,967,143 A | * | 10/1999 | Klappenberger | 128/207.29 |
| 6,109,264 A | * | 8/2000 | Sauer | 128/207.29 |
| 6,298,851 B1 | * | 10/2001 | Parota et al. | 128/207.29 |
| 6,706,017 B1 | * | 3/2004 | Dulguerov | 604/164.01 |
| 6,742,519 B1 | * | 6/2004 | Turnbull | 128/207.29 |

* cited by examiner

*Primary Examiner*—Teena Mitchell
(74) *Attorney, Agent, or Firm*—Brinks Hofer Gilson Lione (57) ABSTRACT

An apparatus and method for performing a percutaneous tracheostomy procedure utilizing dilatation means that do not require entry into the trachea by downward pressure, in order to minimize the risk of posterior tracheal trauma. In addition, the apparatus is structured to facilitate entry of the tracheostomy tube into the dilated entry site without permitting any significant shrinkage or reduction in diameter of the dilated opening.

21 Claims, 6 Drawing Sheets

PERCUTANEOUS TRACHEOSTOMY BALLOON APPARATUS

RELATED APPLICATIONS

The present patent document claims the benefit of the filing date under 35 U.S.C. §119(e) of Provisional U.S. Patent Application Ser. No. 60/465,973, filed Apr. 28, 2003, which is hereby incorporated by reference.

BACKGROUND

1. Technical Field

This invention relates generally to a medical device for percutaneously accessing a patient's air passageway, and more particularly, to a device for atraumatically dilating an opening in a tracheal wall and positioning a tracheal tube in said opening.

2. Background Information

The restoration of an adequate air passageway is the first critical step in maintaining the ability of a seriously ill or injured patient to breathe, or in performing resuscitation on a patient unable to breathe. Endotracheal intubation (the placement of a tube through the nostrils or mouth and into the trachea itself) is the preferred method for establishing an air passageway when the trachea, nostrils and/or mouth are free of obstruction. When such obstruction is present, however, endotracheal intubation is not possible, so that some other passageway for airflow must be established.

The most direct way to provide an air passageway under these circumstances is to form an opening in the tracheal wall, and once formed, to keep it open by inserting a tracheal tube. Conventional tracheal tubes generally include an open distal aperture and a circumferential inflatable cuff to provide a seal between the tracheal wall and the tracheal tube.

Several methods and devices are known for forming or enlarging an opening in a tracheal wall. Each method is subject to its own advantages and drawbacks. For example, tracheostomy and cricothyrotomy procedures have been performed by using a scalpel to make an incision in the neck. Such procedures entail a high degree of surgical skill to perform successfully, particularly since it is vital to locate and avoid unintentional severing of the blood vessels in the area. These procedures can even require the surgeon to cut through several blood vessels and ligate (tie) them to the trachea, in order to achieve an adequately large opening. The length of time needed to perform these procedures (often, on the order of half an hour) is poorly suited to emergency treatment, when prompt restoration of the air passageway is critical. Moreover, the use of a scalpel to fully form an opening potentially causes undue trauma to the tissues surrounding the opening, and can result in the formation of an unduly large or oversized opening in the soft tissue of the neck.

To minimize such trauma, it has been found desirable to initially incise only a small opening, and thereafter enlarge the opening with further dilation. For example, one technique for dilating an opening includes the use of a wire guide to facilitate the introduction of a dilator into the trachea. This technique involves the insertion of a needle and an over-the-needle catheter into the trachea. The needle is removed and the catheter replaced with a wire guide. A tapered, elongated, tubular dilator is positioned over the wire guide and introduced into the trachea. A drawback of this technique is that it requires the preliminary use of a scalpel to make an incision through the skin and cricothyroid membrane so that the needle can be inserted into the trachea. Even though intended to be performed in an emergency situation, the technique entails the sequential manipulation of several devices by the physician, which is time consuming and complicates the procedure.

Another procedure eliminates the use of the catheter and involves placing a wire guide through the needle itself. The opening formed by the needle is then dilated by the use of a device having a handle and a nose, the nose extending laterally from the axis of the handle. The nose has two jaws that spread apart for separating the tissue surrounding the opening, and the device is introduced into the trachea by positioning the elongated, tapered nose over the wire guide. While this type of device offers more powerful dilation than is possible with elongated tubular dilators, a problem with this device is that the unguarded nose must be inserted into the trachea with precision, and must be manipulated at an angle, in order to avoid perforating the posterior tracheal wall.

Another prior art technique for dilating an opening is the use of a tapered, elongated, tubular dilator, or a series of tapered dilators having increasingly larger diameters. Although such dilators are effective for forming a suitably-sized opening in the tracheal wall, each dilator presents a pointed distal end to the posterior tracheal wall when introduced into the trachea. The risk of injury to the trachea is compounded by the toughness of the tracheal membrane, which resists the introduction of medical devices. Introducing these elongated dilators requires the application of considerable force. Although a hydrophilic coating may be applied to the dilator to reduce the amount of force required to insert the dilator, a physician must still exert a downward force to push the dilator into the trachea, and yet avoid puncturing the posterior tracheal wall.

A prior art device described in U.S. Pat. No. 5,653,230, incorporated by reference herein, describes an apparatus and method for radially dilating a tracheal opening. This device permits the enlargement of an opening without risk of perforating the rear of the trachea by providing a polymeric inflatable balloon at the distal end of a catheter. The balloon is inflated to atraumatically dilate a portion of the tracheal wall to form the opening. Although this device is generally effective for avoiding the necessity for the downward or axial force required with many existing devices, the device is structured such that the balloon is deflated immediately following dilation, and is then advanced through the tracheal opening into the interior of the trachea before the tracheostomy tube is inserted into the opening. This leaves the dilated opening unsupported for a period of time. In some patients, this unsupported dilated opening is subject to shrinkage in diameter or even closure. Such action may cause difficulties when the tracheostomy tube is advanced into the opening, resulting in the necessity to re-dilate the opening or to apply a downward force to pass the distal end of the tracheostomy tube through the opening.

It would be desirable to provide an apparatus for forming and dilating an opening in a tracheal wall which is atraumatic, that is, which substantially avoids the trauma and damage to the tracheal wall encountered in many prior methods and devices. It would also be highly desirable to find such an apparatus which permits the enlargement of a tracheal opening without high risk of perforating the rear of the trachea.

BRIEF SUMMARY

The present invention addresses the problems of the prior art by providing an apparatus and method for performing a percutaneous tracheostomy procedure utilizing dilatation means that do not require entry into the trachea by downward pressure, in order to minimize the risk of posterior tracheal trauma. In addition, the apparatus is structured to facilitate entry of the tracheostomy tube into the dilated entry site without permitting any significant shrinkage or reduction in diameter of the dilated opening.

In one embodiment thereof, the present invention comprises an apparatus for providing an airway through a tracheal wall of a patient. The apparatus comprises a balloon catheter having an inflatable balloon at its distal end, the balloon being adapted to atraumatically dilate a portion of the tracheal wall upon inflation. The balloon catheter is aligned with a tracheal tube such that a portion of the balloon catheter extends through a bore in the tracheal tube. A proximal end of the inflatable balloon is distal to and generally adjacent the distal end of the tracheal tube, whereby the tracheal tube is adapted to provide an airway following the atraumatic dilation of the tracheal wall. The inventive apparatus is advanceable into the trachea without relative axial movement between the balloon catheter and the tracheal tube.

In another embodiment thereof, the present invention comprises a method for providing an airway through an opening in the tracheal wall of a patient using an airway apparatus. The apparatus comprises a balloon catheter and a tracheal tube. The balloon catheter includes an inflatable balloon at its distal end, whereby the balloon is adapted to atraumatically dilate a portion of the tracheal wall upon inflation. The tracheal tube is aligned with the balloon catheter such that a portion of the balloon catheter extends through a bore in the tracheal tube bore, and a proximal end of the inflatable balloon is distal to and generally adjacent the distal end of the tracheal tube. A punctured opening is formed in the tracheal wall, and the apparatus is advanced into the punctured opening such that the inflatable balloon is positioned across the punctured opening. The punctured opening is atraumatically dilated by inflating the balloon. The apparatus is then further advanced into the dilated opening while the balloon is inflated such that the tracheal tube opening is positioned across the dilated opening. The balloon is then deflated, and the balloon catheter is withdrawn through the tracheal tube bore. Preferably, the apparatus is advanced into the punctured opening over a wire guide.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

DETAILED DESCRIPTION OF THE DRAWINGS AND THE PRESENTLY PREFERRED EMBODIMENTS

Figures 1, 2:
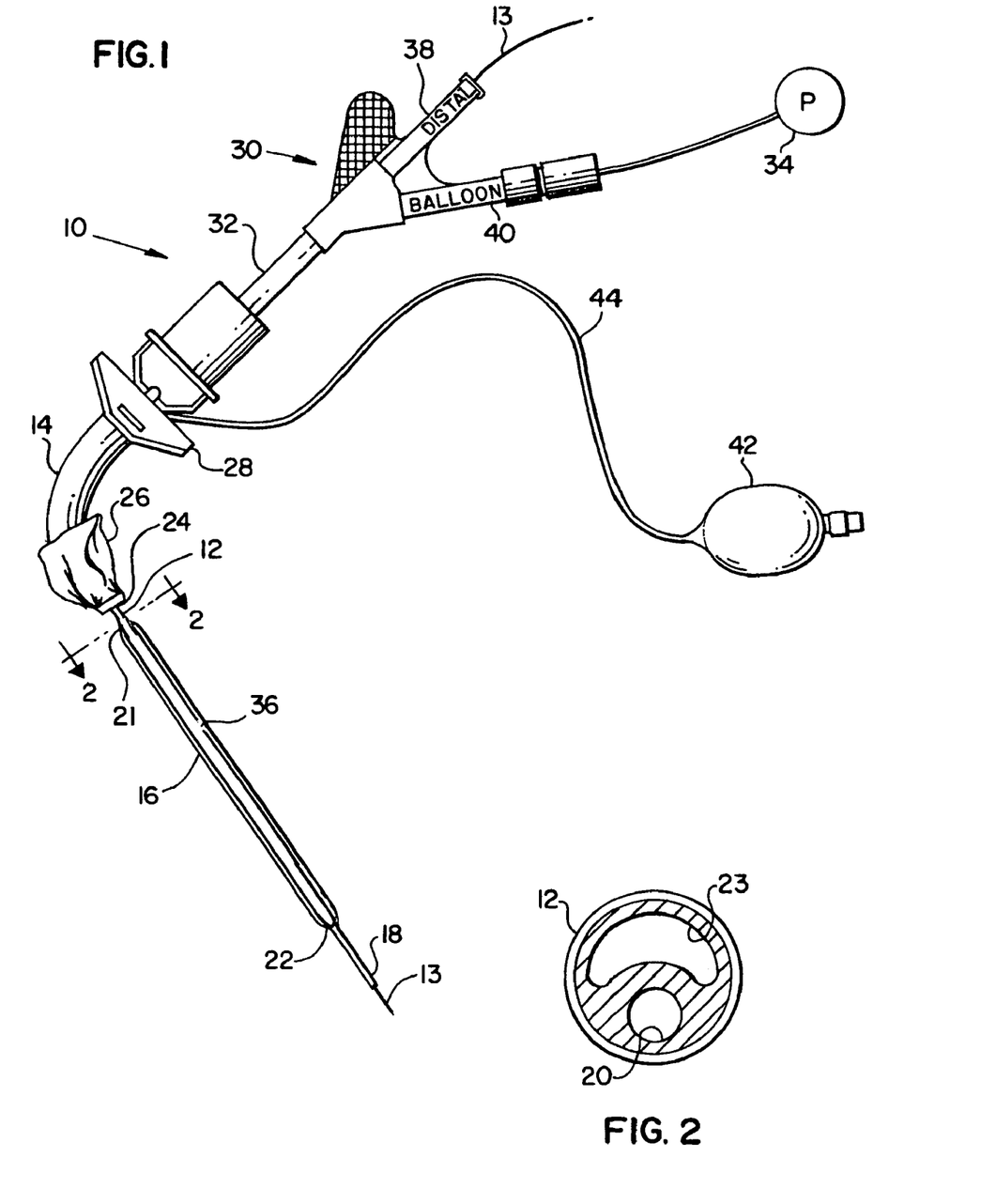
FIG. 1 is a perspective view of a preferred embodiment of the present invention.
FIG. 2 is an enlarged cross-sectional view taken along line 2—2 of FIG. 1.

A preferred embodiment of a percutaneous tracheostomy balloon apparatus 10 of the present invention is illustrated in FIG. 1. Apparatus 10 is used in conjunction with a conventional percutaneous wire guide 13 for positioning a tracheal tube in an opening in the tracheal wall of a patient utilizing the well-known Seldinger technique.

In the embodiment of FIG. 1, apparatus 10 comprises a balloon catheter 12, a tracheal tube (also referred to as a tracheostomy tube) 14, a manifold 30 and a connecting portion 32, such as a stabilizer. Balloon catheter 12 extends from the manifold 30 to the distal end 18 of the device. Balloon catheter 12 includes an inflatable balloon 16, and a perforate atraumatic tip 18 distal to the balloon 16. Preferably, the balloon 16 has a generally cylindrical inflated shape, and includes a proximal end 21 and a distal end 22 that taper with respect to the longitudinal axis of the catheter 12. The inflated diameter of the balloon 16 is selected in view of the size of tracheal opening to be formed. The balloon 16 is preferably between about 30 and 60 mm long.

Catheter 12 is preferably formed of conventional medical grade, synthetic materials such as a polyamide or polyethylene. The balloon 16 is preferably formed of flexible but inelastic materials such as PET or nylon. The balloon 16 can conveniently have an average burst pressure of between about 2 and 6 atmospheres, preferably between about 4 and 6 atmospheres. Those skilled in the art may readily optimize the burst pressure to a desired level. The balloon catheter 12 is adapted for advancement along a wire guide as mentioned above.

The catheter 12 includes a longitudinal throughbore 20 (FIG. 2) dimensioned to receive the wire guide 13 therein. The wire guide 13 will typically have a diameter of about 0.035 to 0.052 inch, and the throughbore is dimensioned to accommodate the wire guide. The tip 18 of the catheter 12 may be tapered in the distal direction but maintains an opening of sufficient size to allow entry of the wire guide into the throughbore 20. The catheter 12 also includes a longitudinally extending bore 23 (FIG. 2) for supplying a fluid under pressure for inflating the balloon 16. The bore 23 is open to a chamber which fluidly connects the bore to a supply of pressurized fluid 34 in well-known fashion, the fluid supply 34 being indicated in FIG. 1 in only a general manner by the symbol "P". A port 36 in catheter 12 is open to the interior of balloon 16 to complete the fluid communication of the balloon 16 with the fluid supply 34. Preferably, the fluid provided by the fluid supply 34 is a conventional fluid, such as saline solution or sterile water, supplied under a pressure of, e.g., about 5 atmospheres, which is adequate to atraumatically dilate the tracheal wall to form a suitable opening. Those skilled in the art can readily optimize the parameters of an inflatable balloon to suit a particular purpose.

The tracheal tube 14 is composed of a medical grade, substantially rigid synthetic material, for example, radiopaque polyvinyl chloride. The tracheal tube 14 possesses a permanent curve which facilitates its introduction into an opening in the tracheal wall. The tracheal tube 14 comprises a distal end 24 having an aperture open to the trachea and lungs of the patient when the device is inserted, as well as an inflatable circumferential cuff 26 positioned adjacent to the distal end 24 of the tracheal tube 14. The distal end of the tracheal tube as shown in FIG. 1 includes a slight taper, however this is not required, and the tube may be generally cylindrical throughout its length if desired. As is conventional, the cuff 26 is desirably a thin wall, high volume, low pressure cuff, composed of a flexible and somewhat elastic material. This permits the cuff 26 to establish a good seal between the tracheal tube 14 and the trachea of the patient upon insertion of the tracheal tube.

The tracheal tube 14 can further include a flange 28 for abutment against the skin of the patient when the tracheal tube 14 is inserted in the tracheal opening. Tracheal tube flanges are well known in the art and can comprise, for example, a flat disk or a conventional swivel neck plate that may be pivotable with respect to the body of the tracheal tube 14. A fluid reservoir 42 is provided to supply low-pressure fluid (such as air) for inflating and deflating the cuff 26, and a conventional tube or conduit 44 is provided to fluidly connect the cuff 26 to the fluid supply 42. The nature of such elements is well known and not critical to the present invention, and therefore will not be further described.

The tracheal tube 14 possesses conventional dimensions suited to the patient into whom it will be introduced. For example, for adult patients, the tracheal tube 14 can typically have an outside diameter of about 8.5 to about 14.0 mm, and an inside diameter of about 6.0 to 10.0 mm. For pediatric patients, the tracheal tube can be made to any smaller dimensions as may be appropriate.

Figure 5:
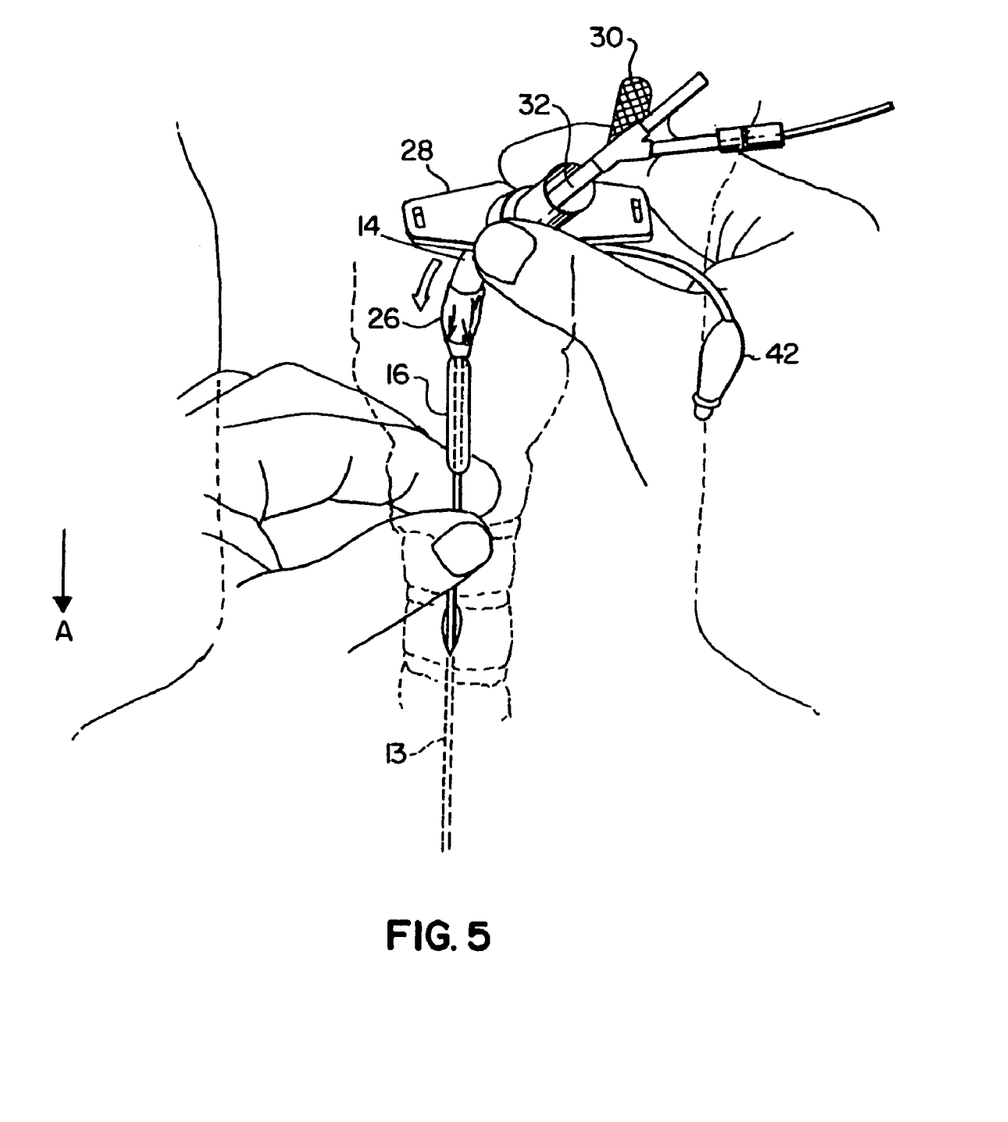
Figure 6:
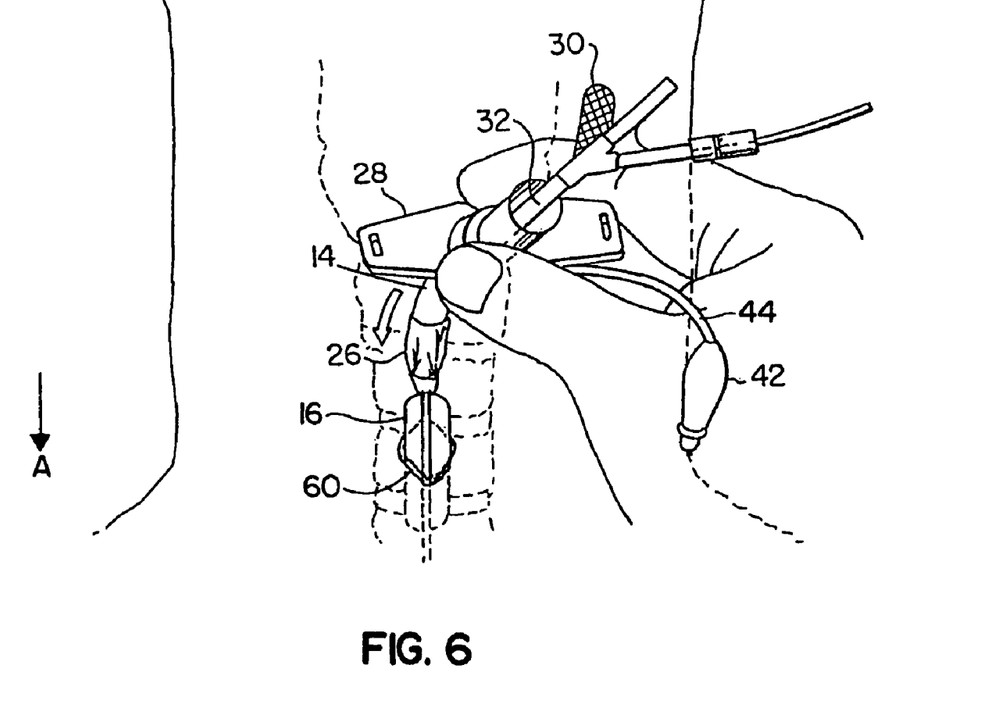
Figure 7:
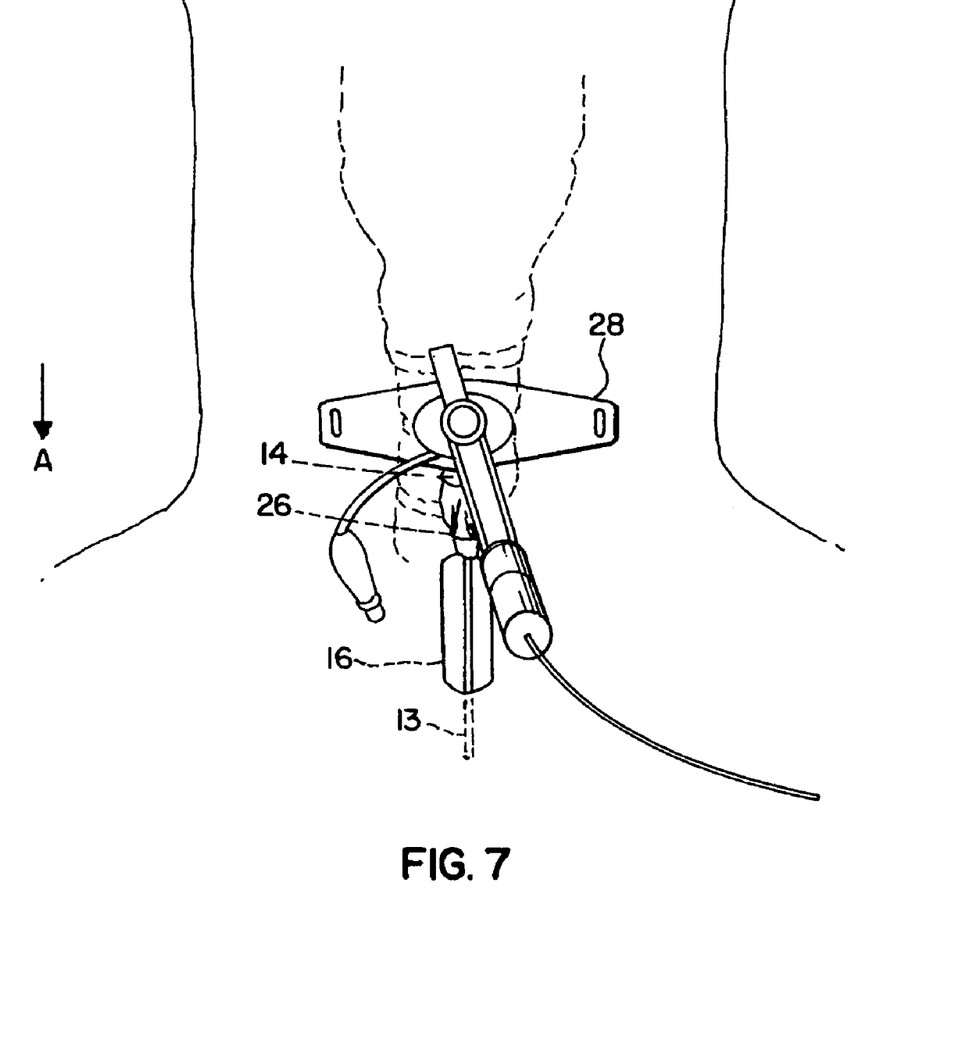

As shown in the figures, the tracheal tube extends longitudinally such that its distal end 24 is generally adjacent to the proximal end 21 of balloon 16. As used herein, "generally adjacent" is meant to indicate that there is little or no gap between the distal end of tracheal tube 14 and the proximal end of balloon 16 when the balloon is inflated. FIG. 1 shows a slight gap between the tracheal tube and the uninflated balloon. In FIGS. 5–7, there is no gap, and the tracheal tube directly abuts the proximal end of the balloon. Although a gap on the order of about 5 cm may be acceptable in some instances and is considered within the scope of this definition, it is preferred that the gap, if present at all, be on order of 2 cm or less, more preferably 1 cm or less, and even more preferably, less than about 5 mm. Most preferably, there will be no gap, and the distal end of the tracheal tube will abut the proximal end of the balloon.

In the preferred embodiment shown, a manifold 30 is provided at the proximal end of the apparatus. In the embodiment shown, manifold includes two arms 38, 40, although other numbers of arms are possible. Arm 38 provides an opening that communicates with distal tip 18 to allow passage of wire guide 13 therethrough. Arm 40 comprises a portion of the pathway between fluid source 34 and the interior of balloon 16. Manifold 30 is conventional in size and shape, and is generally formed of a hard plastic polymer.

In the embodiment of FIG. 1, the connecting portion, such as stabilizer 32, extends from the distal end of manifold 30 to virtually the proximal end 21 of balloon 16. Stabilizer 32 comprises a hollow tubular structure, such as a conventional extruded catheter. Preferably, stabilizer 32 comprises a conventional polymer of the type used in medical applications, such as urethane, polyurethane, polyethylene, polyamide, or a fluorocarbon, having sufficient dimensional stability to provide support to the tracheal tube, as further described. In this embodiment, the stabilizer extends through the longitudinally extending bore of the tracheal tube and provides dimensional support to the tracheal tube. This support enhances the stability of the inventive apparatus as it is advanced through an opening in the tracheal tube wall. The outside diameter of the stabilizer 32 preferably approaches the inside diameter of the tracheal tube 14, so that little clearance exists between the stabilizer and the tracheal tube. A clearance of 1 mm, or even as small as about 0.1 mm or less, may be acceptable for a particular case. Although the stabilizer need not have such a large outside diameter, this relationship adds stability to the apparatus and facilitates the insertion of the tracheal tube. When a tight clearance is provided between the outer diameter of the stabilizer and the inner diameter of the tracheal tube, it may be advantageous to apply a water-soluble jelly or other lubricant over the outer surface of the stabilizer 32 to ensure that the stabilizer can be readily withdrawn from the tracheal tube following insertion of the tracheal tube into the tracheal opening. Preferably, stabilizer 32 is dimensioned such that it extends from the manifold to the distal end of tracheal tube 14, or within about 1–2 cm of that distal end.

Since the tracheal tube 14 is coaxially carried by the stabilizer 32, the stabilizer 32, the balloon catheter 12, the tracheal tube 14, and the manifold 30 (when present) are adapted for advancement along a wire guide together, without any longitudinal movement of any of them relative to one another during such advancement. Such movement as a single unit reduces the number of manipulative steps necessary to introduce the tracheal tube 14 into the opening, thereby making the introduction faster and easier to perform.

As indicated above, the purpose of forming an opening in the tracheal wall is to allow the insertion of tracheal tube 14 through the tracheal wall, so as to establish an air passageway for the patient. It is preferred that the balloon 16, when inflated, have a diameter substantially the same as or greater than the outside diameter of the tracheal tube 14 and the uninflated cuff 26. Preferably, the outer diameter of the inflated balloon may exceed the outer diameter of the tracheal tube and cuff by about 0.5 or 1 mm. Those skilled in the art will recognize that some variation is generally acceptable and will not appreciably affect the operation of apparatus 10.

Thus, for example, for use with the tracheal tube 14 having an outside diameter of 12.0 mm, the balloon 16 should have a diameter when inflated of 12.0 mm, or preferably 0.5 to 1.0 mm more. This close sizing or slight oversizing of the balloon diameter as compared to the tracheal tube diameter ensures that the opening formed by the balloon 16 will be large enough to prevent damage to the cuff 26 during insertion of the tracheal tube 14 into the opening. The balloon may be straight as shown in FIG. 1, or if desired, may be curved to conform to the shape of an opening and/or pathway in which it is to be utilized.

Figure 3:
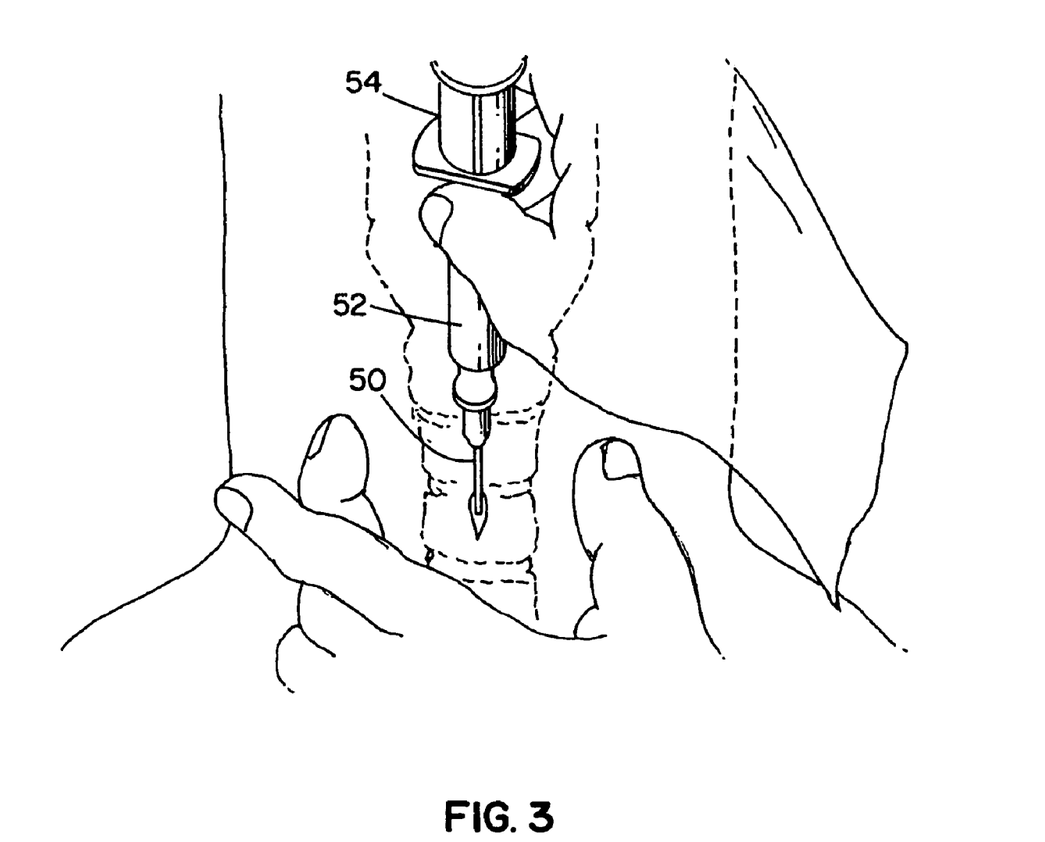
FIGS. 3 through 7 are stepwise views of an insertion procedure performed with the preferred embodiment of the present invention.

The use of the apparatus 10 of the present invention for forming an opening in a tracheal wall will now be described in connection with FIGS. 3 through 7. Initially, the membrane of the tracheal wall is palpated in an appropriate area, such as between the first and second tracheal rings, or between the second and third tracheal rings. A slight incision may be made with a scalpel through the skin and the membrane. A hollow needle 50 carried by a syringe 52 is inserted through the tracheal wall at the incision, as shown in FIG. 3. Gentle back pressure is applied to the plunger 54 of the syringe 52 by drawing back on the plunger 54. A fluid may be contained in the barrel of the syringe 52, and this back pressure causes bubbles to appear in the fluid as a positive visual indication that the needle 50 has fully penetrated the tracheal wall. Some physicians may prefer to initially puncture the skin with a needle, and eliminate the incision step. Still others may prefer to puncture the skin with a needle, insert a wire guide, and then make a longitudinal incision. The inventive apparatus easily accommodates any of these techniques.

Figure 4:
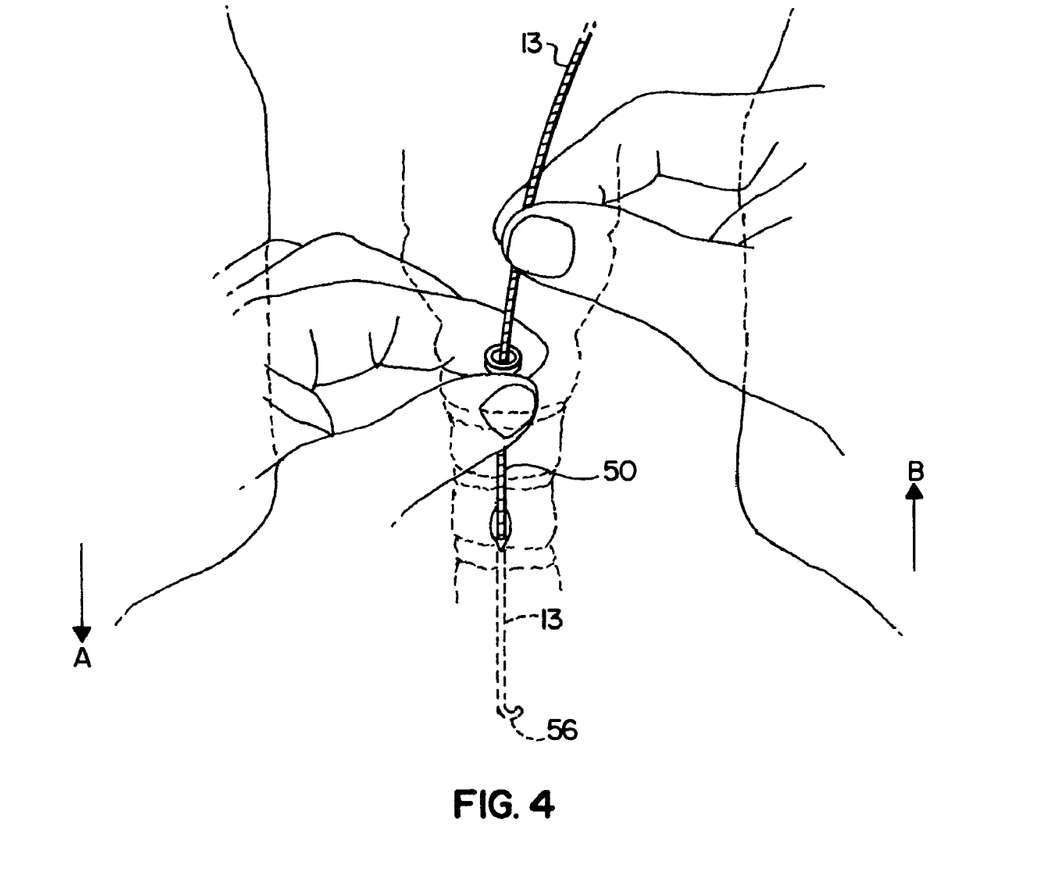

Once verification is obtained that the needle 50 has penetrated the tracheal wall, the syringe 52 is detached from the needle 50, leaving the needle 50 in position across the tracheal wall, as shown in FIG. 4. An atraumatic tip of wire guide 13 is then percutaneously inserted through the tracheal wall as shown in FIG. 4 by passing the atraumatic tip 56 through the interior of the hollow needle 50, in the direction of arrow A. The hollow needle 50 is then removed from the tracheal wall by withdrawing it in the direction of arrow B, while allowing the wire guide 13 to remain in place across the tracheal wall.

The inventive apparatus 10 is then positioned over the wire guide 13, as shown in FIG. 5. Prior to insertion of apparatus, the external surface of uninflated balloon 16 may be coated with copious amounts of a conventional, medical grade, water soluble lubricant. Such positioning is carried out by placing the atraumatic tip 18 of the balloon catheter 12 over the wire guide 13 so that the wire guide 13 is received in the longitudinal throughbore 20 in the catheter 12. The apparatus 10 is then advanced along the wire guide 13 in the direction of arrow A in FIG. 5 until the inflatable balloon 16 of the catheter 12 lies fully across the tracheal wall.

The fluid supply 34 is then activated to provide pressurized fluid through manifold arm 40, the longitudinally extending bore 23, and the port 36, to inflate the balloon 16 to a pressure of, e.g., about 5 atmospheres for a period of about 3–5 seconds. The subcutaneous structures of the tracheal wall are atraumatically dilated in radial fashion, thereby forming opening 60 in the tracheal wall, as shown in FIG. 6.

Once opening 60 is formed, the apparatus 10 is immediately advanced with the balloon still inflated, downward into the trachea, in the direction of arrow A in FIG. 7. The presence of the lubricant on the outside of balloon 16 enables the balloon to be readily passed through tracheal opening 60, without becoming stuck or otherwise hung up on the opening.

The tracheal tube 14 is positioned across the opening 60 by advancing the apparatus 10 along the wire guide 13 until the flange 28 on the tracheal tube 14 abuts the skin over the tracheal opening 60. Such advancement is carried out without longitudinal movement of the balloon catheter, tracheal tube 14 and stabilizer 32 relative to one another. Movement of these elements together is advantageous because the inflated balloon 16 and the tracheal tube 14 provide a smooth and substantially constant-diameter transition for insertion of the tracheal tube 14.

If the balloon 16 had been deflated prior to the advancement of the tracheal tube 14, or if there was a significant drop-off in diameter of portions of apparatus 10 disposed between the balloon 16 and the tracheal tube 14, the advancement of the apparatus through tracheal opening 60 would leave the opening unsupported between the time that the inflatable balloon was deflated (or otherwise passed into the trachea) and the time that the tracheal tube 14 was positioned across the tracheal opening 60. In such event, the tracheal opening 60 may begin to retract or shrink, thus hindering the smooth insertion of the tracheal tube 14. In addition, such shrinkage may undesirably necessitate the use of an axial force to advance the tracheal tube 14 into the opening. By maintaining the balloon in its inflated condition throughout the advancement of the apparatus, and by eliminating the significant gap (in the axial direction) that existed in prior art devices between the balloon and the tracheal tube, apparatus 10 is structured to provide a relatively constant-diameter structure to support the tracheal opening 60 throughout the advancement of apparatus 10. Thus, the use of apparatus 10 enables tracheal opening 60 to achieve its dilated condition and to maintain that condition throughout the advancement of the apparatus into the opening, until tracheal tube 14 is properly positioned across the tracheal wall.

When the tracheal tube 14 is in proper position across the tracheal opening 60 (FIG. 7), it can be secured in place by suture and standard neck wrap in conventional fashion. The balloon 16 can now be deflated, and the remaining portions of apparatus 10 withdrawn in a proximal direction, leaving only tracheal tube 14 in position across the tracheal wall. The tracheal tube cuff 26 may now be inflated to establish a seal between the tracheal tube 14 and the trachea of the patient in conventional fashion. Proper placement of the tracheal tube 14 may be confirmed by capnography. If desired, a conventional intubation inner sleeve and stabilizer (not shown) can be inserted into the tracheal tube 14 for the usual and well-known purposes.

It is highly desirable that the fit of the tracheal tube 14 in the tracheal opening 60 be relatively tight. Of course, it is also desirable that the circumferential cuff 26 of the tracheal tube 14 not be damaged during its passage through the tracheal opening 60. Therefore, the method is preferably carried out with a balloon 16 whose diameter, when inflated, is equal to or slightly greater (e.g., about 1 mm greater) than the combined diameter of the tracheal tube 14 and the diameter of the uninflated cuff 26. The insertion of the tracheal tube 14 can be aided by application of an appropriate water-soluble lubricant to the outside of the stabilizer 32, and to the outside of the tracheal tube 20 and cuff 24 before insertion.

In another embodiment, connecting portion 32 need not comprise a discrete stabilizer element as described above. Rather, balloon catheter 12 can be extruded or otherwise formed to have a large diameter proximal portion 32 and a smaller diameter distal portion 18. The large diameter proximal portion includes bores 20 and 23 as described (FIG. 2). In this embodiment, the large diameter portion of balloon catheter 12 extends to the distal end of tracheal tube 14, preferably within about 1–2 cm of the distal end. This portion provides the size, strength and support otherwise provided by the stabilizer of the previous embodiment.

Although the description provided above use indicates the use of a manifold in the inventive apparatus, those skilled in the art will recognize that a discrete manifold element is not necessary. Rather, manifold 30 is simply provided as a convenient mechanism to control the placement and passage of the wire guide and the introduction of the inflation fluid for the balloon. Any other convenient way of providing for these tasks may be substituted, such alternatives being well within the knowledge of one of ordinary skill in the art. As merely one such example, balloon catheter 12 can be structured to include suitable conduits to accomplish the tasks of the manifold.

It may be desirable to visualize placement of the balloon under bronchioscope visualization. This visualization may provide for optimal dilation while maximizing the patency of the airway. A bronchoscope can be passed into an endotracheal tube in conventional fashion to facilitate withdrawal of the tube to just below the vocal cords. After placement of the endotracheal tube, the anterior neck anatomy is defined by physical examination, and a sterile marker may be used to identify the midline. A wire guide can then be inserted as before, followed by the inventive apparatus 10 over the wire guide. The lubricant-coated balloon is inflated to the desired pressure for the predetermined time period to dilate the subcutaneous structures, and the tracheal tube 14 is then immediately advanced into the trachea under bronchoscopic guidance. The tube may then be secured in place with a conventional neck strap as previously described. The use of a bronchoscope in tracheal visualization is a well-known technique, and need not be further described.

As another variation of the invention, a conventional introducer sheath, such as a 12 French splittable sheath may be used to initially introduce the apparatus into a tracheal opening to be dilated. An introducer sheath may facilitate the placement of the balloon in certain instances. When the introducer sheath is used, the balloon is placed into the introducer over the wire guide, and the introducer is then split or peeled away.

It should be evident from the above discussion that the apparatus 10 of the present invention can comprise not only the combination of the balloon catheter 12 and the tracheal tube 14, but also can comprise one or more of a manifold, a stabilizer 32, a wire guide 13, and a hollow needle 50. A splittable introducer sheath can also be included if desired.

The method and apparatus of the present invention is advantageous over the prior methods and devices for forming or dilating tracheal openings. The present invention allows the opening to be formed and dilated atraumatically without risk of perforating the posterior wall of the trachea. In addition, the apparatus is structured to provide support to the tracheal opening to enable it to maintain its dilated condition prior to insertion of the tracheal tube.

Any undisclosed details of the construction or composition of the various elements of the disclosed embodiment of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

The present invention is useful in the performance of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting essentially of the disclosed parts and steps.

What is claimed is:

1. An apparatus for providing an airway through a tracheal wall of a patient, comprising:
    a balloon catheter having a proximal end and a distal end, said balloon catheter including an inflatable balloon at said distal end, said balloon adapted to atraumatically dilate a portion of said tracheal wall upon inflation; and
    a tracheal tube having a proximal end, a distal end, and a bore extending longitudinally therethrough, said tracheal tube and said balloon catheter aligned such that a portion of said balloon catheter extends through said tracheal tube bore and a proximal end of the inflatable balloon is distal to and spaced from said distal end of said tracheal tube by a distance not exceeding about 2 cm, said tracheal tube adapted to provide said airway following said atraumatic dilation of said tracheal wall, wherein said apparatus is advanceable into said trachea without relative axial movement between said balloon catheter and said tracheal tube.

2. The apparatus of claim 1, wherein said balloon upon inflation has an outer diameter substantially the same as the outer diameter of the tracheal tube.

3. The apparatus of claim 2, wherein said balloon outer diameter does not vary from the tracheal tube outer diameter by more than about 1 mm.

4. The apparatus of claim 1, wherein said distance is less than about 1 cm.

5. The apparatus of claim 1, wherein said proximal end of said balloon abuts said distal end of said tracheal tube.

6. The apparatus of claim 1, further comprising a stabilizer having a proximal end, a distal end, and a passageway extending therethrough, a distal portion of said stabilizer extending substantially through said tracheal tube bore and providing dimensional support to said tracheal tube, said stabilizer and said balloon catheter aligned such that a portion of said balloon catheter extends through said passageway.

7. The apparatus of claim 6, wherein at least the portion of said stabilizer that extends through the tracheal tube has an outside diameter that does not vary from the inside diameter of the tracheal tube by more than about 1 mm.

8. The apparatus of claim 7, wherein the portion of said stabilizer that extends through the tracheal tube has an outside diameter that does not vary from said inside diameter by more than about 0.1 mm.

9. The apparatus of claim 1, wherein said balloon catheter comprises a large diameter proximal portion and a small diameter distal portion, wherein said large diameter portion comprises said portion of the balloon catheter that extends substantially through said tracheal tube bore, said large diameter portion providing dimensional support to said tracheal tube and having an outside diameter that does not vary from the inside diameter of the tracheal tube by more than about 1 mm.

10. An apparatus for restoring an airway in a patient, comprising:
    a manifold;
    a stabilizer extending from a distal end of said manifold, the stabilizer including a lumen therethrough;
    a tracheal tube carried by said stabilizer; and
    a balloon catheter extending from the distal end of the manifold and extending through said lumen, the balloon catheter including an inflatable balloon distal to said stabilizer, a proximal end of said balloon being spaced from a distal end of said tracheal tube by a distance not exceeding about 2 cm, the balloon adapted to atraumatically dilate an opening in the tracheal wall of a patient when the balloon is in an inflated condition, said apparatus being advanceable along a wire guide such that said balloon is positionable in said tracheal opening for said dilation, and being further advanceable when the balloon is in the inflated condition such that said tracheal tube is positionable across said tracheal opening for restoring said airway.

11. The apparatus of claim 10, wherein said tracheal tube and said balloon in said inflated condition each have an outer diameter, said respective outer diameters being substantially similar such that said apparatus has a relatively constant outer diameter as it is advanced along said guide wire.

12. The apparatus of claim 11, wherein said respective outer diameters do not vary by more than about 1 mm.

13. The apparatus of claim 10 wherein said apparatus includes a clearance space between an outer diameter of said stabilizer and an inner diameter of said tracheal tube, said clearance space not exceeding about 1 mm.

14. The apparatus of claim 10, wherein said inflatable balloon is coated with a lubricant.

15. A method for providing an airway through an opening in the tracheal wall of a patient, comprising the steps of:

providing an airway apparatus, said airway apparatus comprising a balloon catheter and a tracheal tube; said balloon catheter having a proximal end, a distal end and a throughbore extending therethrough, and including an inflatable balloon at said distal end, said balloon adapted to atraumatically dilate a portion of said tracheal wall upon inflation; said tracheal tube having a proximal end, a distal end, and a bore extending longitudinally therethrough, said tracheal tube and said balloon catheter aligned such that a portion of said balloon catheter extends through said tracheal tube bore and a proximal end of the inflatable balloon is distal to and generally adjacent said distal end of said tracheal tube;

forming a punctured opening in said tracheal wall;

advancing the apparatus into said punctured opening such that said inflatable balloon is positioned across said punctured opening;

dilating said punctured opening by inflating said balloon;

further advancing said apparatus into said dilated opening while said balloon is inflated such that said tracheal tube is positioned across said dilated opening;

deflating said balloon; and withdrawing the balloon catheter through said tracheal tube bore.

16. The method of claim 15, further comprising:

percutaneously inserting a distal end of a wire guide into the trachea through said puncture, and positioning said apparatus over a proximal end of said wire guide so that the wire guide passes through said throughbore;

advancing the apparatus into said punctured opening over the wire guide to position the inflatable balloon across the puncture; and further advancing the apparatus the over the wire guide while the balloon is inflated to position the tracheal tube across the dilated opening.

17. The method of claim 16, wherein said inflatable balloon is coated with a lubricant prior to advancing said balloon across said puncture.

18. The method of claim 16, wherein said apparatus further comprises a stabilizer, wherein a distal portion of said stabilizer extends through said tracheal tube bore to provide dimensional support to said tracheal tube.

19. The method of claim 16, wherein said balloon catheter comprises a large diameter proximal portion and a small diameter distal portion, wherein said large diameter portion comprises said portion of the balloon catheter that extends substantially through said tracheal tube bore, said large diameter portion providing dimensional support to said tracheal tube.

20. The method of claim 15, wherein the proximal end of the inflatable balloon is spaced from the distal end of the tracheal tube by a distance not exceeding about 1 cm.

21. The method of claim 15, wherein the proximal end of the inflatable balloon abuts the distal end of the tracheal tube.

* * * * *